US009850540B2

(12) United States Patent
An et al.

(10) Patent No.: US 9,850,540 B2
(45) Date of Patent: Dec. 26, 2017

(54) METHOD FOR DETECTING LUNG CANCER USING LUNG CANCER-SPECIFIC METHYLATION MARKER GENE

(75) Inventors: Sung Whan An, Daejeon (KR); Young Ho Moon, Daejean (KR); Tae Jeong Oh, Daejeon (KR)

(73) Assignee: GENOMICTREE, INC., Daejeon (KR)

( * ) Notice: Subject to any disclaimer, the term of this patent is extended or adjusted under 35 U.S.C. 154(b) by 590 days.

(21) Appl. No.: 12/922,184

(22) PCT Filed: Feb. 18, 2009

(86) PCT No.: PCT/KR2009/000777
§ 371 (c)(1),
(2), (4) Date: Oct. 7, 2010

(87) PCT Pub. No.: WO2009/113771
PCT Pub. Date: Sep. 17, 2009

(65) Prior Publication Data
US 2011/0027796 A1 Feb. 3, 2011

(30) Foreign Application Priority Data
Mar. 14, 2008 (KR) .................. 10-2008-0023685

(51) Int. Cl.
| C12Q 1/70 | (2006.01) |
| C12P 19/34 | (2006.01) |
| C07H 21/04 | (2006.01) |
| C12Q 1/68 | (2006.01) |

(52) U.S. Cl.
CPC ...... *C12Q 1/6886* (2013.01); *C12Q 2600/112* (2013.01); *C12Q 2600/154* (2013.01); *C12Q 2600/156* (2013.01)

(58) Field of Classification Search
None
See application file for complete search history.

(56) References Cited

U.S. PATENT DOCUMENTS

| 5,541,308 A * | 7/1996 | Hogan et al. .............. 536/23.1 |
| 7,871,774 B2 | 1/2011 | Yoon et al. |
| 2007/0264659 A1 | 11/2007 | An et al. |
| 2009/0264306 A1 | 10/2009 | Caldwell et al. |
| 2009/0305256 A1 * | 12/2009 | Pfeifer et al. ................. 435/6 |

FOREIGN PATENT DOCUMENTS

| CN | 1820785 A | 8/2006 |
| KR | 1020060027893 A | 3/2006 |

OTHER PUBLICATIONS

Verma et al. (Critical Review in Oncology/Hematology 60 (2006), pp. 9-18).*
Jones et al. (Nature Reviews, 2002, vol. 3, pp. 415-428).*
Smiraglia et al. (Human Molecular Genetics 2001 vol. 10, pp. 1413-1419).*
Feinberg (Nature Reviews, 2004, vol. 4, pp. 143-153.*
Cottrell (Clin. Biochem. 37(2004) 595-604).*
Buck et al (Biotechniques (1999) 27(3):528-536).*
Ahlquist, D.A., et al., Colorectal cancer screening by detection of altered human DNA in stool: feasibility of a multitarget assay panel, Gastroenterology, 2000, pp. 1219-1227, vol. 119.
Esteller, M., et al. Detection of Aberrant Promoter Hypermethylation of Tumor Suppressor Genes in Serum DNA from Non-Samll Cell Lung Cancer Patients, Cancer Research, Jan. 1, 1999, pp. 67-70, vol. 59.
Kopreski, M.S., et al., Detection of Tumor Messenger RNA in the Serum of Patients with Malignant Melonoma, Clinical Cancer Research, Aug. 1999, pp. 1961-1965, vol. 5.
Miyashiro, I., et al., Molecular Strategy for Detecting Metastatic Cancers with Use of Multiple Tumor-Specific MAGE-A Genes, Clinical Chemistry, 2001, pp. 505-512, vol. 47, No. 3.
Palmisano, W.A., et al., Predicting Lung Cancer by Detecting Aberrant Promoter Methylation in Sputum, Cancer Research, Nov. 1, 2000, pp. 5954-5958, vol. 60.
Sanchez-Cespedes, M., et al., Gene Promoter Hypermethylation in Tumors and Serum of Head and Neck Cancer Patients, Cancer Research, Feb. 15, 2000, pp. 892-895, vol. 60.
Schena, M., et al, Quantitative Monitoring of Gene Expression Patterns with a Complementary DNA Microarray, Science, Oct. 20, 1995, pp. 467-470, vol. 270, No. 5235.
Sueoka, E., et al., Heterogeneous Nuclear Ribonucleoprotein B1 as a New Marker of Early Detection for Human Lung Cancers, Cancer Research, Apr. 1, 1999, pp. 1404-1407, vol. 59.
Taylor, Kristen H., et al., Large-Scale CpG Methylation Analysis Identifies Novel Candidate Genes and Reveals Methylation Hotspots in Acute Lymphoblastic Leukemia, Cancer Research, 2007, pp. 2617-2625, vol. 67, No. 6.
Homo sapiens chromosome 5 genomic contig, GRCh37.p@ reference primary assembly, NCBI Reference Sequence: NT_029289.11.
Lu, Y. et al.; "A gene expression signature predicts survival of patients with stage I non-small cell lung cancer," PLOS MED., 2006, pp. 2229-2242, vol. 3, Issue 12
Goo, Young AH, et al.; "Stromal mesenchyme cell genes of the human prostate and bladder," BMC Urology, 2005, pp. 1-11, vol. 5, Issue 17.
U.S. Appl. No. 60/969,157 to Pfeifer et al., Filed Aug. 30, 2007.
Sakaguchi, M., et al.; "Frequent suppression of protocadherin gene expression in small cell lung carcinoma cell lines," Proceedings of the American Association for Cancer Research Annual Meeting, 1999, pp. 133, Reference Not Attached as This Reference Cannot Be Located; See the Supplemental European Search Report for a Brief Description of the Relevance of This Reference.

(Continued)

Primary Examiner — Sarae L Bausch
(74) Attorney, Agent, or Firm — Hultquist, PLLC; Steven J. Hultquist

(57) ABSTRACT

The present invention relates to a method for detecting lung cancer using a lung cancer-specific biomarker, and more particularly to a biomarker for lung cancer diagnosis, which can detect methylation of PCDHGA12 gene whose 5'UTR or exon 1 region is specifically methylated in lung cancer cells, and to a method of detecting lung cancer and the stage of its progression using the biomarker. The diagnostic kit according to the present invention makes it possible to diagnose lung cancer at an early stage in an accurate and rapid manner compared to conventional methods and can be used for prognosis and monitoring of lung cancer and the stage of its progression.

6 Claims, 4 Drawing Sheets

(56) References Cited

OTHER PUBLICATIONS

Sungwhan, AN et al.; "Identification of hypermethylation of PCDHGA12 gene by genome-wide analysis as a novel diagnostic marker of lung cancer," Proceedings of the American Association for Cancer Research Annual Meeting, 2009, Abstract.

Moon, Young Ho, et al.; "Methylated DNA Isolation Assay-Mediated DNA Methylation Detection and Whole-Genome Methylation Profiling," American biotechnology Laboratory, 2009, pp. 23-25, vol. 27, Issue 10; Eference Not Attached As This Reference Cannot Be Located; See the Supplemental European Search Report for a Brief Description of the Relevance of This Reference.

International Search Report in International Patent Application No. PCT/KR2009/000777, dated Jun. 11, 2009, by the Korean Intellectual Property Office serving as the International Searching Authority.

Supplemental European Search Report in European Patent Application No. EP 09 72 0916, date of completion of the report May 24, 2011.

Lu, Yan, et al., "A Gene Expression Signature Predicts Survival of Patients with Stage I Non-Small Cell Lung Cancer," PLOS Medicine, 2006, pp. 2229-2243, vol. 3.

Chinese Office Action for Application No. 200980108952.2 dated May 16, 2014.

Brock, M. V., et al., "DNA Methylation Markers and Early Recurrence in Stage I Lung Cancer", "The New England Journal of Medicine", Mar. 13, 2008, pp. 1118-1128, vol. 358.

* cited by examiner

A

SEQUENCE LISTING

```
<160> NUMBER OF SEQ ID NOS: 21

<210> SEQ ID NO 1
<211> LENGTH: 1620
<212> TYPE: DNA
<213> ORGANISM: Homo sapiens

<400> SEQUENCE: 1
ctattaaagc gaatacggta gatttccatc ccctttttgaa gaacagtagg tggagctatt      60
taagatataa aaacgaaata tcctttctgg gagttcaaga ttgtgcagta attggttagg     120
```

```
actctgagcg ccgctgttca ccaatcgggg agagaaaagc ggagatcctg ctcgccttgc      180
acgcgcctga agcacaaagc agatagctag gaatgaacca tccctgggag tatgtggaaa      240
caacggagga gctctgactt cccaactgtc ccattctatg ggcgaaggaa ctgctcctga      300
cttcagtggt taagggcaga attgaaaata attctggagg aagataagaa tgattcctgc      360
gcgactgcac cgggactaca aagggcttgt cctgctggga atcctcctgg ggactctgtg      420
ggagaccgga tgcacccaga tacgctattc agttccggaa gagctggaga aaggctctag      480
ggtgggcgac atctccaggg acctggggct ggagccccgg gagctcgcgg agcgcggagt      540
ccgcatcatc cccagaggta ggacgcagct tttcgccctg aatccgcgca gcggcagctt      600
ggtcacggcg ggcaggatag accgggagga gctctgtatg ggggccatca agtgtcaatt      660
aaatctagac attctgatgg aggataaagt gaaaatatat ggagtagaag tagaagtaag      720
ggacattaac gacaatgcgc cttactttcg tgaaagtgaa ttagaaataa aaattagtga      780
aaatgcagcc actgagatgc ggttccctct accccacgcc tgggatccgg atatcgggaa      840
gaactctctg cagagctacg agctcagccc gaacactcac ttctccctca tcgtgcaaaa      900
tggagccgac ggtagtaagt accccgaatt ggtgctgaaa cgcgccctgg accgcgaaga      960
aaaggctgct caccacctgg tccttacggc ctccgacggg ggcgacccgg tgcgcacagg     1020
caccgcgcgc atccgcgtga tggttctgga tgcgaacgac aacgcaccag cgtttgctca     1080
gcccgagtac cgcgcgagcg ttccggagaa tctggccttg gcacgcagc tgcttgtagt      1140 caacgctacc gaccctgacg aaggagtcaa tgcggaagtg aggtattcct tccggtatgt     1200
ggacgacaag gcggcccaag ttttcaaact agattgtaat tcagggacaa tatcaacaat     1260
aggggagttg gaccacgagg agtcaggatt ctaccagatg gaagtgcaag caatggataa     1320
tgcaggatat tctgcgcgag ccaaagtcct gatcactgtt ctggacgtga acgacaatgc     1380
cccagaagtg gtcctcacct ctctcgccag ctcggttccc gaaaactctc ccagagggac     1440
attaattgcc ctttaaatg taaatgacca agattctgag gaaaacggac aggtgatctg     1500
tttcatccaa ggaaatctgc cctttaaatt agaaaaatct tacggaaatt actatagttt     1560
agtcacagac atagtcttgg atagggaaca ggttcctagc tacaacatca cagtgaccgc     1620
```

<210> SEQ ID NO 2
<211> LENGTH: 482
<212> TYPE: DNA
<213> ORGANISM: Homo sapiens

<400> SEQUENCE: 2

```
cccctttga agaacagtag gtggagctat ttaagatata aaaacgaaat atcctttctg       60
ggagttcaag attgtgcagt aattggttag gactctgagc gccgctgttc accaatcggg      120
gagagaaaag cggagatcct gctcgccttg cacgcgcctg aagcacaaag cagatagcta      180
ggaatgaacc atccctggga gtatgtggaa acaacggagg agctctgact tcccaactgt      240
cccattctat gggcgaagga actgctcctg acttcagtgg ttaagggcag aattgaaaat      300
aattctggag gaagataaga atgattcctg cgcgactgca ccgggactac aaagggcttg      360
tcctgctggg aatcctcctg gggactctgt gggagaccgg atgcacccag atacgctatt      420
cagttccgga gagctggag aaaggctcta gggtgggcga catctccagg gacctggggc      480
tg                                                                     482
```

<210> SEQ ID NO 3
<211> LENGTH: 598

```
<212> TYPE: DNA
<213> ORGANISM: Homo sapiens

<400> SEQUENCE: 3
gcttgtcctg ctgggaatcc tcctggggac tctgtgggag accggatgca cccagatacg    60
ctattcagtt ccggaagagc tggagaaagg ctctagggtg ggcgacatct ccagggacct   120
ggggctggag ccccgggagc tcgcggagcg cggagtccgc atcatcccca gaggtaggac   180
gcagcttttc gccctgaatc cgcgcagcgg cagcttggtc acggcgggca ggatagaccg   240
ggaggagctc tgtatggggg ccatcaagtg tcaattaaat ctagacattc tgatggagga   300
taaagtgaaa atatatggag tagaagtaga agtaagggac attaacgaca atgcgcctta   360
ctttcgtgaa agtgaattag aaataaaaat tagtgaaaat gcagccactg agatgcggtt   420
ccctctaccc cacgcctggg atccggatat cgggaagaac tctctgcaga gctacgagct   480
cagcccgaac actcacttct ccctcatcgt gcaaaatgga gccgacggta gtaagtaccc   540
cgaattggtg ctgaaacgcg ccctggaccg cgaagaaaag gctgctcacc acctggtc    598

<210> SEQ ID NO 4
<211> LENGTH: 638
<212> TYPE: DNA
<213> ORGANISM: Homo sapiens

<400> SEQUENCE: 4
gaaaaggctg ctcaccacct ggtccttacg gcctccgacg ggggcgaccc ggtgcgcaca    60
ggcaccgcgc gcatccgcgt gatggttctg gatgcgaacg acaacgcacc agcgtttgct   120
cagcccgagt accgcgcgag cgttccggag aatctggcct tgggcacgca gctgcttgta   180
gtcaacgcta ccgaccctga cgaaggagtc aatgcggaag tgaggtattc cttccggtat   240
gtggacgaca aggcggccca agtttttcaaa ctagattgta attcagggac aatatcaaca   300 atagggagt tggaccacga ggagtcagga ttctaccaga tggaagtgca agcaatggat   360
aatgcaggat attctgcgcg agccaaagtc ctgatcactg ttctggacgt gaacgacaat   420
gccccagaag tggtcctcac ctctctcgcc agctcggttc ccgaaaactc tcccagaggg   480
acattaattg cccttttaaa tgtaaatgac caagattctg aggaaaacgg acaggtgatc   540
tgtttcatcc aaggaaatct gccctttaaa ttagaaaaat cttacggaaa ttactatagt   600
ttagtcacag acatagtctt ggatagggaa caggttcc                           638

<210> SEQ ID NO 5
<211> LENGTH: 30
<212> TYPE: DNA
<213> ORGANISM: Artificial Sequence
<220> FEATURE:
<223> OTHER INFORMATION: Synthetic Construct

<400> SEQUENCE: 5 tttttttga agaatagtag gtggagttat                                      30

<210> SEQ ID NO 6
<211> LENGTH: 24
<212> TYPE: DNA
<213> ORGANISM: Artificial Sequence
<220> FEATURE:
<223> OTHER INFORMATION: Synthetic Construct

<400> SEQUENCE: 6
caaccccaaa tccctaaaaa tatc                                           24
```

<210> SEQ ID NO 7
<211> LENGTH: 25
<212> TYPE: DNA
<213> ORGANISM: Artificial Sequence
<220> FEATURE:
<223> OTHER INFORMATION: Synthetic Construct

<400> SEQUENCE: 7
gtttgttttg ttgggaattt ttttg                                              25

<210> SEQ ID NO 8
<211> LENGTH: 27
<212> TYPE: DNA
<213> ORGANISM: Artificial Sequence
<220> FEATURE:
<223> OTHER INFORMATION: Synthetic Construct

<400> SEQUENCE: 8
aaccaaataa taaacaacct tttcttc                                            27

<210> SEQ ID NO 9
<211> LENGTH: 28
<212> TYPE: DNA
<213> ORGANISM: Artificial Sequence
<220> FEATURE:
<223> OTHER INFORMATION: Synthetic Construct

<400> SEQUENCE: 9
gaaaaggttg tttattattt ggtttta                                            28

<210> SEQ ID NO 10
<211> LENGTH: 30
<212> TYPE: DNA
<213> ORGANISM: Artificial Sequence
<220> FEATURE:
<223> OTHER INFORMATION: Synthetic Construct

<400> SEQUENCE: 10
aaaacctatt ccctatccaa aactatatct                                         30

<210> SEQ ID NO 11
<211> LENGTH: 21
<212> TYPE: DNA
<213> ORGANISM: Artificial Sequence
<220> FEATURE:
<223> OTHER INFORMATION: Synthetic Construct

<400> SEQUENCE: 11
gggagagaaa agtggagatt t                                                  21

<210> SEQ ID NO 12
<211> LENGTH: 24
<212> TYPE: DNA
<213> ORGANISM: Artificial Sequence
<220> FEATURE:
<223> OTHER INFORMATION: Synthetic Construct

<400> SEQUENCE: 12
ctcccaaaaa taattcattc ctaa                                               24

<210> SEQ ID NO 13
<211> LENGTH: 22
<212> TYPE: DNA
<213> ORGANISM: Artificial Sequence
<220> FEATURE:
<223> OTHER INFORMATION: Synthetic Construct

```
<400> SEQUENCE: 13
aactatctac tttatacttc aa                                               22

<210> SEQ ID NO 14
<211> LENGTH: 26
<212> TYPE: DNA
<213> ORGANISM: Artificial Sequence
<220> FEATURE:
<223> OTHER INFORMATION: Synthetic Construct

<400> SEQUENCE: 14
ggataaagtg aaaatatatg gagtag                                           26

<210> SEQ ID NO 15
<211> LENGTH: 23
<212> TYPE: DNA
<213> ORGANISM: Artificial Sequence
<220> FEATURE:
<223> OTHER INFORMATION: Synthetic Construct

<400> SEQUENCE: 15
ccaaataata aacaaccttt tct                                              23

<210> SEQ ID NO 16
<211> LENGTH: 20
<212> TYPE: DNA
<213> ORGANISM: Artificial Sequence
<220> FEATURE:
<223> OTHER INFORMATION: Synthetic Construct

<400> SEQUENCE: 16
gtgaaaatgt agttattgag                                                  20

<210> SEQ ID NO 17
<211> LENGTH: 22
<212> TYPE: DNA
<213> ORGANISM: Artificial Sequence
<220> FEATURE:
<223> OTHER INFORMATION: Synthetic Construct

<400> SEQUENCE: 17
agaaaaggtt gtttattatt tg                                               22

<210> SEQ ID NO 18
<211> LENGTH: 19
<212> TYPE: DNA
<213> ORGANISM: Artificial Sequence
<220> FEATURE:
<223> OTHER INFORMATION: Synthetic Construct

<400> SEQUENCE: 18
tacccaaaac caaattctc                                                   19

<210> SEQ ID NO 19
<211> LENGTH: 20
<212> TYPE: DNA
<213> ORGANISM: Artificial Sequence
<220> FEATURE:
<223> OTHER INFORMATION: Synthetic Construct

<400> SEQUENCE: 19
tgtttattat ttggttttta                                                  20

<210> SEQ ID NO 20
```

```
<211> LENGTH: 20
<212> TYPE: DNA
<213> ORGANISM: Artificial Sequence
<220> FEATURE:
<223> OTHER INFORMATION: Synthetic Construct

<400> SEQUENCE: 20
gaagaaaagg ctgctcacca                                              20

<210> SEQ ID NO 21
<211> LENGTH: 19
<212> TYPE: DNA
<213> ORGANISM: Artificial Sequence
<220> FEATURE:
<223> OTHER INFORMATION: Synthetic Construct

<400> SEQUENCE: 21
tcgcatccag aaccatcac                                               19
```

METHOD FOR DETECTING LUNG CANCER USING LUNG CANCER-SPECIFIC METHYLATION MARKER GENE

CROSS-REFERENCE TO RELATED APPLICATIONS

This application is filed under the provisions of 35 U.S.C. §371 and claims the priority of International Patent Application No. PCT/KR2009/000777 filed on 18 Feb. 2009 entitled "Method for Detecting Lung Cancer Using Lung Cancer-Specific Methylation Marker Gene" in the name of Sung Whan A N et al., which claims priority of Korean Patent Application No. 10-2008-00023685 filed on 14 Mar. 2008, both of which are hereby incorporated by reference herein in their entirety.

TECHNICAL FIELD

The present invention relates to a method for detecting lung cancer using a lung cancer-specific biomarker, and more particularly to a biomarker for lung cancer diagnosis, which can detect methylation of PCDHGA12 gene whose 5'UTR or exon 1 region is specifically methylated in transformed lung cancer cells, and to a method of detecting lung cancer and the stage of its progression using the biomarker.

BACKGROUND ART

Lung cancer was a very rare disease before cigarette smoking became common in the 20$^{th}$ century. The incidence of lung cancer has increased rapidly, and in Western countries, lung cancer is the most frequent cancer in both men and women. In Korea, lung cancer frequently occurs in men, and its incidence in women is also dramatically increasing. This increase in the incidence of lung cancer is attributable to increases in cigarette smoking, air pollution and industrial pollution and so on.

Even at the present time when medical science has advanced, the 5-year survival rate of cancer patients, particularly solid tumor patients (other than blood cancer patients) is less than 50%, and about ⅔ of all cancer patients are diagnosed at an advanced stage and almost all die within 2 years after cancer diagnosis. Such poor results in cancer therapy are not only the problem of therapeutic methods, but also due to the fact that it not easy to diagnose cancer at an early stage and to accurately diagnose advanced cancer and to carry out the follow-up of cancer patients after cancer therapy.

Recently, genetic testing methods have actively been attempted to diagnose cancer. Among them, a typical method is to use PCR to determine whether or not the ABL:BCR (Abelson Murine Leukemia Viral Oncogene Homolog: Breakpoint cluster region) fusion gene that is a genetic indicator of leukemia is present in blood. Furthermore, another method has been attempted, in which the presence of genes expressed by cancer cells is detected by RT-PCR and blotting, thereby diagnosing cancer cells present in blood cells. However, this method has shortcomings in that it can be applied only to some cancers, including prostate cancer and melanoma, has a high false positive rate. Also it is difficult to standardize detection and reading in this method, and its utility also limiter (Kopreski, M. S. et al., *Clin. Cancer Res.*, 5:1961, 1999; Miyashiro, I. et al., *Clin. Chem.*, 47:505, 2001). In addition, genetic testing using a DNA in serum or plasma has recently been actively attempted. The use of DNA isolated from cancer to analyze cancer-specific gene abnormalities, such as the mutation, deletion and functional loss oncogenes and tumor-suppressor genes, allows the diagnosis of cancer.

Meanwhile, a method is being attempted in which the presence of cancer cells or oncogenes in the sputum or bronchoalveolar lavage fluid of lung cancer patients is detected by a gene or antibody test (Palmisano, W. A. et al., *Cancer Res.*, 60:5954, 2000; Sueoka, E. et al., *Cancer Res.*, 59:1404, 1999). However, in order to accurately diagnose cancers that involve a large number of gene abnormalities and show various mutations, a method capable of simultaneously analyzing a large number of genes in an accurate and automatic manner is required, but such a method has not yet been established.

Accordingly, methods of diagnosing cancer by measuring DNA methylation have recently been proposed. DNA methylation occurs mainly at cytosines of CpG islands in the promoter region of a specific gene, and thus the binding of a transcription factor is hindered so that the expression of a specific gene is silenced. Thus, analysis of the methylation of the promoter CpG island of tumor-suppressor genes is very helpful in cancer research. An active attempt has been made to analyze the methylation of the promoter CpG island by methods such as methylation-specific PCR (hereinafter, referred to as "MSP") or automatic base sequencing and to use the analysis results for the diagnosis and screening of cancer.

Although there are disputes about whether the methylation of promoter CpG islands directly induces oncogenesis or causes secondary changes in oncogenesis, it has been confirmed that tumor suppressor genes, DNA repair genes, cell cycle regulator genes and the like in various cancers are hyper-methylationed so that the expression of these genes is silenced. Particularly, it is known that the hyper-methylation of the promoter region of a specific gene occurs in the early stage of oncogenesis.

Accordingly, the promoter methylation of tumor-related genes is an important indicator of cancer and can be used in many applications, including the diagnosis and early detection of cancer, the prediction of the risk of oncogenesis, the prediction of the prognosis of cancer, follow-up examination after treatment, and the prediction of a response to anticancer therapy. Indeed, an attempt has recently been actively made to examine the promoter methylation of tumor-related genes in blood, sputum, saliva, feces or urine and to use the examination results for the diagnosis and treatment of various cancers (Esteller, M. et al., *Cancer Res.*, 59:67, 1999; Sanchez-Cespedez, M. et al., *Cancer Res.*, 60:892, 2000; Ahlquist, D. A. et al., *Gastroenterol.*, 119:1219, 2000).

Currently, the diagnosis of lung cancer is possible by various examinations, and if a symptom suspected of lung cancer exists, chest X-ray examination, microscopic examination, video examination, biopsy, examination of metastasis or the like is performed to determine whether the symptom is lung cancer and to determine the degree of progression of lung cancer. However, this detection method requires an expensive system, is costly, has difficulty and is not suitable for the early diagnosis of lung cancer, and in addition, there is difficulty in sampling. Thus, in view of the fact that the 5-year survival rate of stage I lung cancer patients having a tumor size of less than 3 cm reaches about 70%, diagnosing lung cancer at an early stage when the size of the lesion is small is the best method. Accordingly, it is urgently required to develop a detection method which is more efficient than various existing lung cancer detection methods. Namely, it is required to develop a novel lung cancer-specific biomarker which can diagnose lung cancer at an early stage, treat large volumes of samples and has high sensitivity and specificity.

Accordingly, the present inventors filed and received a patent for a microarray and kit for cancer diagnosis including the colon cancer-specific expression-decreased genes LAMA2 (laminin merosin alpha 2), FABP4 (fatty acid binding protein 4), GSTA2 (glutathione S-transferase A2), STMN2 (stathmin-like 2), NR4A2 (nuclear receptor subfamily 4, group A, member 2), DSCR1L1 (down syndrome critical region gene 1-like 1), A2M(alpha-2-macroglobulin) and SEPP1(selenoprotein P, plasma, 1) (Korean Patent Registration No. 10-0617649).

The present inventors have made many efforts to develop a diagnostic kit capable of effectively diagnosing lung cancer and, as a result, have found that lung cancer and the stage of its progression can be diagnosed by measuring the degree of methylation using the methylated 5'UTR or methylated exon 1 region of PCDHGA12 (GenBank NM_032094) gene, which is specifically methylated in lung cancer cells, as a lung cancer-specific biomarker, thereby completing the present invention.

SUMMARY OF INVENTION

It is an object of the present invention to provide a biomarker for lung cancer diagnosis containing a methylated region of a gene which is specifically methylated in lung cancer.

Another object of the present invention is to provide a method of detecting lung cancer and the stage of its progression using a biomarker for lung cancer diagnosis.

To achieve the above objects, the present invention provides a biomarker for lung cancer diagnosis comprising the methylated 5'UTR or exon 1 region of the lung cancer-specific expression-decreased gene PCDHGA12 (GenBank NM_032094, protocadherin gamma subfamily A, 12).

The present invention also provides a biomarker for lung cancer diagnosis, which contains one or more methylated CpG islands and is represented by any one base sequence of SEQ ID NOs: 2 to 4.

The present invention also provides a method for detecting lung cancer or the stage of its progression, the method comprising the steps of: (a) isolating DNA from a clinical sample; and (b) detecting methylation of the 5'UTR or exon 1 region of the lung cancer-specific gene PCDHGA12 (GenBank NM_032094, protocadherin gamma subfamily A, 12) in the isolated DNA.

Other features and embodiments of the present invention will be more apparent from the following description and the appended claims.

DETAILED DESCRIPTION OF THE INVENTION, AND PREFERRED EMBODIMENTS

Figure 1:
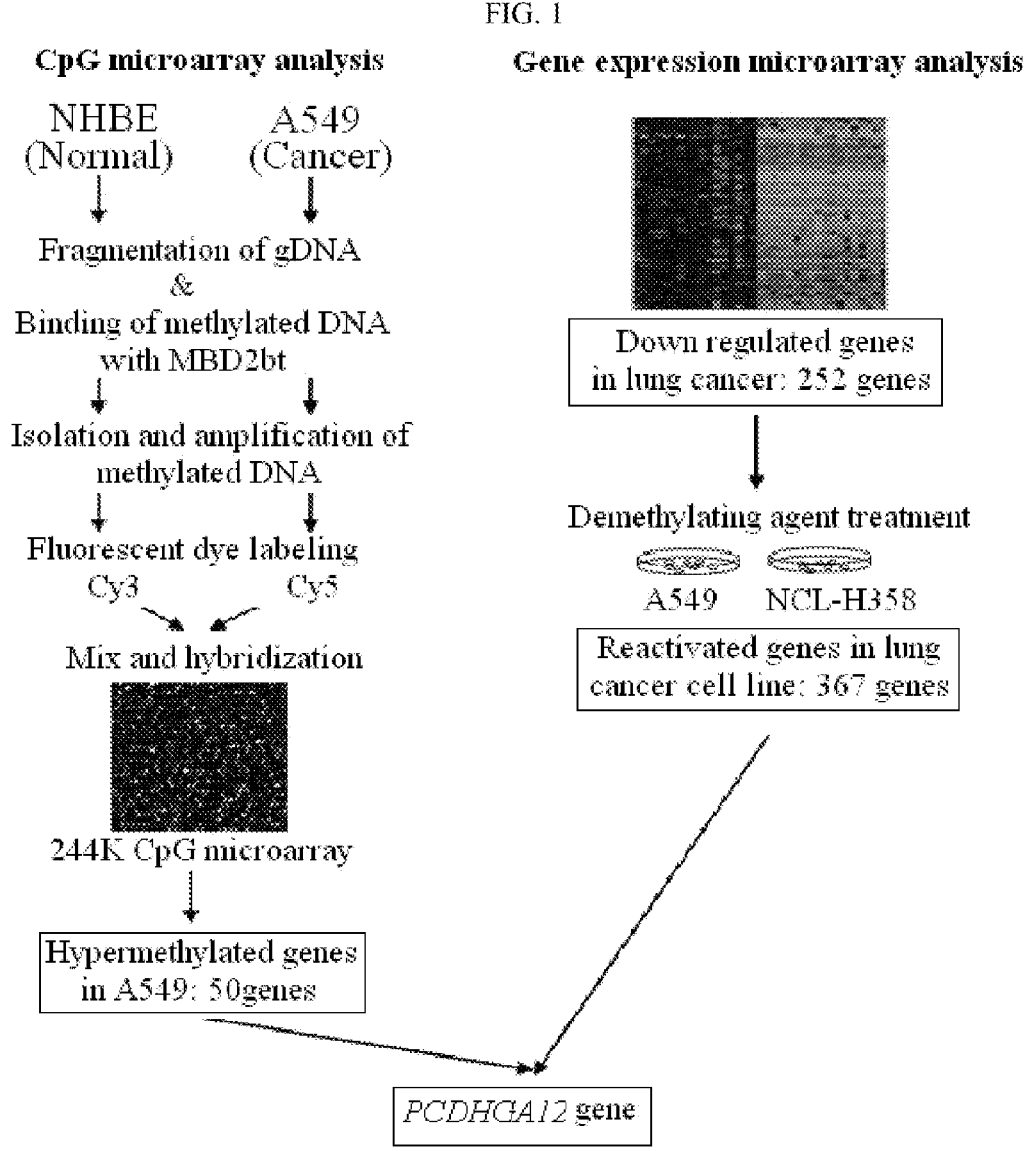
FIG. 1 is a schematic diagram showing a process of discovering the methylation biomarker PCDHGA12 for lung cancer diagnosis.

In one aspect, the present invention relates to a biomarker for lung cancer diagnosis comprising the methylated 5'UTR or methylated exon 1 region of the lung cancer-specific expression-decreased gene PCDHGA12(GenBank NM_032094, protocadherin gamma subfamily A, 12).

In the present invention, the methylated 5'UTR (untranslated region) or methylated exon 1 region preferably contains at least one methylated CpG dinucleotide, and the 5'UTR and exon 1 regions are preferably represented by SEQ ID NO: 1.

An example of a method of screening a methylation marker gene may be a method comprising the steps of: (1) selecting DNA-hypermethylated genes only from a transformed cell line among a transformed cell line and a non-transformed cell line; (2) comparing gene expression profiles of the transformed lung cancer cells and the non-transformed cells adjacent thereto, and generating a list of genes which are more highly expressed in the non-transformed cells; (3) treating the transformed lung cancer line with a methylation inhibitor, and generating a list of genes which are more highly expressed in the transformed lung cancer cell line treated with the methylation inhibitor, compared to non-treated transformed lung cancer cell line; and (4) comparing the gene lists obtained in steps (1), (2) and (3), and regarding a gene, present in all the three lists, as a marker gene which is regulated by methylation in the genome of cells being converted from a non-transformed state to a transformed lung cancer cell form.

In the present invention, the lung cancer-specific expression-decreased gene PCDHGA12 screened from the genomic DNA of lung cancer cell lines by the above screening method has methylated CpG islands in the 5'UTR and exon 1 regions.

In another aspect the present invention relates to a biomarker, which contains one or more methylated CpG islands and is represented by any one base sequence of SEQ ID NOs: 2 and 3.

In the present invention, the DNA fragment is preferably derived from the lung cancer-specific expression-decreased gene PCDHGA12 (GenBank NM_032094, protocadherin gamma subfamily A, 12).

In the present invention, the 5'UTR and exon 1 regions of the lung cancer-specific expression-decreased gene PCDHGA12 has methylation at R1 (SEQ ID NO: 2), R2 (SEQ ID NO: 3) and R3 (SEQ ID NO: 4) regions in the lung cancer cell line.

In one Example of the present invention, the R1, R2 and R3 of PCDHGA12 gene in the lung cancer tissues from lung cancer patients showed very high methylation levels, and the methylation of the R1 region in paired lung cancer tissues and normal tissues adjacent thereto was shown to be high in of 40 clinical samples (i.e., 85% of the clinical samples), and the methylation of the R3 region in these tissues was high in 36 of clinical samples (i.e., 90% of the clinical samples). This suggests that lung cancer can be efficiently diagnosed by measuring the hypermethylation of the R1, R2 and R3 regions of PCDHGA12 gene.

In another aspect, the present invention relates to a method for detecting lung cancer or the stage of its progression, the method comprising the steps of: (a) isolating DNA from a clinical sample; and (b) detecting methylation of the 5'UTR or exon 1 region of PCDHGA12 (GenBank NM_032094, protocadherin gamma subfamily A, 12) gene in the isolated DNA.

In the present invention, the detection of methylation is preferably performed in a DNA region having a sequence selected from the group consisting of SEQ ID NO: 1, SEQ ID NO: 2, SEQ ID NO: 3 and SEQ ID NO: 4.

In the present invention, the detection of methylation is preferably performed using a method selected from the group consisting of PCR, methylation-specific PCR, real-time methylation-specific PCR, PCR using methylated DNA-specific binding proteins, quantitative PCR, a DNA chip-based detection method, pyrosequencing and bisulfite sequencing, and the clinical sample is a tissue, cell, blood or urine from a patient suspected of cancer or a subject to be diagnosed.

By a method of screening methylation biomarker genes, used in Examples of the present invention, not only lung cancer, but also genes which are differentially methylated at various dysplastic stages of tissue that progresses to lung cancer, can be screened. The screened genes can be used for lung cancer screening, risk-assessment, prognosis, disease identification, the diagnosis of disease stages, and the selection of therapeutic targets.

The identification of genes that are methylated in lung cancer and abnormalities at various stages of lung cancer makes it possible to early diagnose lung cancer in an accurate and effective manner and allows methylation profiling of multiple genes and the identification of new targets for therapeutic intervention. Furthermore, the methylation data according to the present invention may be combined with other non-methylation related biomarker detection methods to obtain a more accurate system for lung cancer diagnosis.

According to the method of the present invention, the progression of lung cancer at various stages or phases can be diagnosed by determining the methylation stage of one or more nucleic acid biomarkers obtained from a sample. By comparing the methylation stage of a nucleic acid isolated from a sample at each stage of lung cancer with the methylation stage of one or more nucleic acids isolated from a sample in which there is no cell proliferative abnormality of lung tissue, a specific stage of lung cancer in the sample can be detected. Herein, the methylation stage may be hypermethylation.

In one embodiment of the present invention, nucleic acid may be methylated in the regulatory region of a gene. In another embodiment, a gene which is involved in cell transformation can be diagnosed by detecting methylation outside of the regulatory region of the gene, because methylation proceeds inwards from the outside of the gene.

In yet another embodiment of the present invention, the abnormal growth (dysplasia) of lung tissue cells in a sample can be diagnosed by detecting the methylation state of the 5'UTR and exon 1 regions of PCDHGA12 (NM_032094, protocadherin gamma subfamily A, 12) gene using a kit.

The use of the diagnostic kit of the present invention can determine the abnormal growth (dysplastic progression) of lung tissue cells in a sample. The diagnostic method of the present invention comprises determining the methylation state of one or more nucleic acids isolated from a sample, wherein the methylation stage of said one or more nucleic acids is compared with the methylation stage of a nucleic acid isolated from a sample in which there is no abnormal growth (dysplasia) of lung tissue cells.

In still another embodiment of the present invention, the use of the methylated gene marker allows early diagnosis of cells that are likely to form lung cancer. When a gene determined to be methylated in cancer cells is methylated in clinically or morphologically normal-appearing cells, this indicates that the normal-appearing cells progress to carcinogenesis. Thus, lung cancer can be diagnosed at an early stage by detecting the methylation of the 5'UTR and exon 1 region of a lung cancer-specific gene in normal-appearing cells.

The use of the methylated marker gene of the present invention allows detection of the abnormal growth (dysplastic progression) of lung tissue cells in a sample. The detection method of the present invention comprises bringing a sample comprising at least one nucleic acid isolated from a clinical sample into contact with at least one agent capable of determining the methylation state of the nucleic acid, wherein the methylation of the nucleic acid differs from the methylation state of the same region of a nucleic acid preset in a sample in which there is no abnormal growth (dysplastic progression) of lung cells.

In yet another embodiment of the present invention, the likelihood of progression of lung cancer can be diagnosed by examining the methylation of the 5'UTR and exon 1 region of the marker gene in a sample showing a normal phenotype using the above-described kit. The sample may be solid or liquid tissue, cells, urine, serum or plasma.

In the present invention, the method of detecting the methylation of the 5'UTR and exon 1 regions of PCDHGA12 gene comprises the steps of: (a) isolating sample DNA from a clinical sample; (b) treating the isolated DNA with bisulfite; (c) amplifying the treated DNA using primers capable of amplifying a fragment comprising the CpG of the 5'UTR and exon 1 regions of PCDHGA12 gene; and (d) subjecting the product amplified in step (c) to pyrosequencing to determine the methylation of the PCDHGA12 gene.

In one embodiment of the present invention, the detection method can be carried out using a kit. The kit that is used in the present invention comprises: carrier means compartmentalized to receive a sample therein; and one or more containers including a first container containing a reagent that sensitively cleaves unmethylated cytosine, a second container containing primers for amplifying a CpG-containing nucleic acid, and a third containing a means for detecting the presence of a cleaved or uncleaved nucleic acid. The primers that are used in the present invention include sequences set forth in SEQ ID NOs: 5 to 21, and any functional combination and fragments thereof. The carrier means are suited for containing one or more container means such as vials, tubes, and the like, each of the container means comprising one of the separate elements to be used in the method of the present invention. In view of the description provided herein of the inventive method, those of skill in the art can readily determine the apportionment of the necessary reagents among the container means. For example, one of the container means can comprise a container containing a methylation-sensitive restriction enzyme. One or more container means can also include a primer complementary to the nucleic acid locus of interest. In addition, one or more container means can also contain an isoschizomer of said methylation sensitive restriction enzyme.

In still embodiment of the present invention, the method of detecting lung cancer using the kit comprises the steps of: (1) isolating genomic DNA from a clinical sample; (2) treating the isolated genomic DNA with a methylation-sensitive restriction enzyme; (3) amplifying the treated genomic DNA using primers capable of amplifying the biomarker for lung cancer diagnosis of the present invention; and (4) determining the presence or absence of the biomarker for lung cancer diagnosis in the product amplified. In the method, a sample in which the biomarker fragment is present can be diagnosed as lung cancer or a lung cancer progression stage. In order to determine the presence or absence of a PCR amplification product, the kit may additionally contain a fragment capable of hybridizing with the biomarker for lung cancer diagnosis under strict conditions.

Also, methods of determining the presence or absence of the biomarker for lung cancer diagnosis, which can be used in the present invention, include bisulfite sequencing, pyrosequencing, methylation-specific PCR, MethyLight, PCR using methylated DNA binding proteins, and DNA chip assays.

As used herein, the term "cell transformation" refers to the change in characteristics of a cell from one form to another form such as from normal to abnormal, non-tumorous to tumorous, undifferentiated to differentiated, stem cell to non-stem cell. Furthermore, the transformation may be recognized by the morphology, phenotype, biochemical characteristics and the like of a cell.

As used herein, the term "early detection" of cancer refers to discovering the likelihood of cancer prior to metastasis, and preferably before observation of a morphological change in a tissue or cell. Furthermore, the term "early detection" of cell transformation refers to the high probability of a cell to undergo transformation in its early stages before the cell is morphologically designated as being transformed.

As used herein, the term "hypermethylation" refers to the methylation of a CpG island. As used herein, the term "sample" or "clinical sample" is referred to in its broadest sense, and includes any biological sample obtained from an individual, body fluid, a cell line, a tissue culture, depending on the type of assay that is to be performed. Methods for obtaining tissue biopsies and body fluids from mammals are well known in the art. A tissue biopsy of the lungs is a preferred source.

Screening of Methylation Biomarker

In the present invention, there was screened a biomarker gene methylated when a cell or tissue was transformed or when the cell morphology changed. As used herein, the term "transformation" refers to the change in morphology of a cell or tissue from one form to another form such as from normal to abnormal state, non-tumorous to timorous state, or undifferentiated to differentiated state.

Accordingly to the present invention, a biomarker gene methylated in transformation into lung cancer cells was systematically screened. For example, the method of screening the biomarker gene may be a method comprising the steps of: (1) selectively isolating only methylated DNAs from a transformed cell line and a non-transformed cell line using the methylation-specific binding protein MBD2bt; (2) amplifying each of the DNAs and labeling the amplified DNAs with a fluorescent dye; (3) hybridizing each of the labeled DNAs to a microarray capable of measuring methylation; (4) selecting genes hypermethylated in the transformed cells, based on the results of the hybridization; (5) comparing gene expression profiles of transformed lung cancer cells and non-transformed cells adjacent thereto, and generating a list of genes which are more highly expressed in the non-transformed cells; (6) treating the transformed lung cancer line with a methylation inhibitor, and generating a list of genes which are more highly expressed in the treated transformed lung cancer compared to the non-treated transformed lung cancer line; and (7) comparing the gene profiles obtained in steps (5) and (6), and regarding a gene, present in all the three gene lists, as a marker gene which is regulated by methylation in the genome of cells being converted from a non-transformed state to a transformed lung cancer cell form.

The term "nucleic acid" or "nucleic acid sequence" as used herein refers to an oligonucleotide, nucleotide or polynucleotide, or fragments thereof, or single-stranded or double-stranded DNA or RNA of genomic or synthetic origin, sense- or antisense-strand DNA or RNA of genomic or synthetic origin, peptide nucleic acid (PNA), or any DNA-like or RNA-like material of natural or synthetic origin. It is apparent to those of skill in the art, when the nucleic acid is RNA, the deoxynucleotides A, G, C, and T are replaced by the ribonucleotides A, G, C, and U, respectively.

Any nucleic acid may be used in the present invention, given the presence of differently methylated CpG islands can be detected therein. The CpG island is a CpG-rich region in a nucleic acid sequence.

Methylation

In the present invention, any nucleic acid sample, in purified or nonpurified form, can be used, provided it contains or is suspected of containing, a nucleic acid sequence containing a target locus (e.g., CpG-containing nucleic acid). One nucleic acid region capable of being differentially methylated is a CpG island, a sequence of nucleic acid with an increased density relative to other nucleic acid regions of the dinucleotide CpG. The CpG doublet occurs in vertebrate DNA at only about 20% of the frequency that would be expected from the proportion of G*C base pairs. In certain regions, the density of CpG doublets reaches the predicted value; it is increased by ten-fold relative to the rest of the genome. CpG islands have an average G*C content of about 60%, compared with the 40% average in bulk DNA. The islands take the form of stretches of DNA typically about one to two kilobases long. There are about 45,000 islands in the human genome.

In many genes, the CpG islands begin just upstream of a promoter and extend downstream into the transcribed region. Methylation of a CpG island at a promoter usually suppresses expression of the gene. The islands can also surround the 5' region of the coding region of the gene as well as the 3' region of the coding region. Thus, CpG islands can be found in multiple regions of a nucleic acid sequence including upstream of coding sequences in a regulatory region including a promoter region, in the coding regions (e.g., exons), downstream of coding regions in, for example, enhancer regions, and in introns.

In general, the CpG-containing nucleic acid is DNA. However, the inventive method may employ, for example, samples that contain DNA, or DNA and RNA containing mRNA, wherein DNA or RNA may be single-stranded or double-stranded, or a DNA-RNA hybrid may be included in the sample.

A mixture of nucleic acids may also be used. The specific nucleic acid sequence to be detected may be a fraction of a larger molecule or can be present initially as a discrete molecule, so that the specific sequence constitutes the entire nucleic acid. It is not necessary that the sequence to be studied be present initially in a pure form; the nucleic acid may be a minor fraction of a complex mixture, such as contained in whole human DNA. Nucleic acids contained in a sample used for detection of methylated CpG islands may be extracted by a variety of techniques such as that described by Sambrook, et al. (Molecular Cloning: A Laboratory Manual, Cold Spring Harbor, N.Y., 1989).

A nucleic acid can contain a regulatory region which is a region of DNA that encodes information or controls transcription of the nucleic acid. Regulatory regions include at least one promoter. A "promoter" is a minimal sequence sufficient to direct transcription, and renders promoter-dependent gene expression controllable for cell-type specific, tissue-specific, or inducible by external signals or agents. Promoters may be located in the 5' or 3' region of the gene. The number of nucleic acids in all or part of promoter regions can be used to measure CG-island methylation. Moreover, it is generally recognized that methylation of the target gene promoter proceeds naturally from the outer boundary inward. Therefore, an early stage of cell conversion can be detected by analyzing methylation in these outer areas of the promoter region.

Nucleic acids isolated from a subject are obtained in a biological sample from the subject. If it is desired to detect lung cancer or stages of lung cancer progression, the nucleic acid may be isolated from lung tissue by scraping or biopsy. Such samples may be obtained by various medical procedures known to those of skill in the art.

As used herein, the term "hypermethylation" indicates that the methylation at a specific CpG location of tumor cells or in a specific base sequence region consisting of CpG islands is higher than that in normal cells.

Sample

The present invention describes early detection of lung cancer and employs lung cancer-specific gene methylation. The present inventors have found that lung cancer-specific gene methylation also occurs in tissue adjacent to the tumor region. Therefore, in a method for early detection of lung cancer, any sample, including liquid or solid tissue, may be examined for the presence of methylation of the lung cancer-specific gene. Such samples include, but not limited to, sputum, serum or plasma.

Method for Detection of Methylation

Detection of Differential Methylation—Methylation-Specific PCR

When genomic DNA is treated with bisulfite, cytosine in the 5'-CpG'-3 region remains intact, if it was methylated, but the cytosine changes to uracil, if it was unmethylated. Accordingly, based on the base sequence converted after bisulfite treatment, PCR primer sets corresponding to a region having the 5'-CpG-3' base sequence are constructed. Herein, the constructed primer sets are two kinds of primer sets: a primer set corresponding to the methylated base sequence, and a primer set corresponding to the unmethylated base sequence. When genomic DNA is converted with bisulfite and then amplified by PCR using the above two kinds of primer sets, the PCR product is detected in the PCR mixture employing the primers corresponding to the methylated base sequence, if the genomic DNA was methylated, but the genomic DNA is detected in the PCR mixture employing the primers corresponding to the unmethylated, if the genomic DNA was unmethylated. This methylation can be quantitatively analyzed by agarose gel electrophoresis.

Detection of Differential Methylation—Real-Time Methylation Specific PCR

Real-time methylation-specific PCR is a real-time measurement method modified from the methylation-specific PCR method and comprises treating genomic DNA with bisulfite, designing PCR primers corresponding to the methylated base sequence, and performing real-time PCR using the primers. Methods of detecting the methylation of the genomic DNA include two methods: a method of detection using a TanMan probe complementary to the amplified base sequence; and a method of detection using Sybergreen. Thus, the real-time methylation-specific PCR allows selective quantitative analysis of methylated DNA. Herein, a standard curve is plotted using an in vitro methylated DNA sample, and a gene containing no 5'-CpG-3' sequence in the base sequence is also amplified as a negative control group for standardization to quantitatively analyze the degree of methylation.

Detection of Differential Methylation—Pyrosequencing

The pyrosequencing method is a quantitative real-time sequencing method modified from the bisulfite sequencing method. Similarly to bisulfite sequencing, genomic DNA is converted by bisulfite treatment, and then, PCR primers corresponding to a region containing no 5'-CpG-3' base sequence are constructed. Specifically, the genomic DNA is treated with bisulfite, amplified using the PCR primers, and then subjected to real-time base sequence analysis using a sequencing primer. The degree of methylation is expressed as a methylation index by analyzing the amounts of cytosine and thymine in the 5'-CpG-3' region.

Detection of Differential Methylation—PCR Using Methylated DNA-Specific Binding Protein, Quantitative PCR, and DNA Chip Assay When a protein binding specifically only to methylated DNA is mixed with DNA, the protein binds specifically only to the methylated DNA. Thus, either PCR using a methylation-specific binding protein or a DNA chip assay allows selective isolation of only methylated DNA. Genomic DNA is mixed with a methylation-specific binding protein, and then only methylated DNA was selectively isolated. The isolated DNA is amplified using PCR primers corresponding to the promoter region, and then methylation of the DNA is measured by agarose gel electrophoresis.

In addition, methylation of DNA can also be measured by a quantitative PCR method, and methylated DNA isolated with a methylated DNA-specific binding protein can be labeled with a fluorescent probe and hybridized to a DNA chip containing complementary probes, thereby measuring methylation of the DNA. Herein, the methylated DNA-specific binding protein may be, but not limited to, McrBt.

Detection of Differential Methylation—Methylation-Sensitive Restriction Enzyme

Detection of differential methylation can be accomplished by bringing a nucleic acid sample into contact with a methylation-sensitive restriction endonuclease that cleaves only unmethylated CpG sites.

In a separate reaction, the sample is further brought into contact with an isoschizomer of the methylation-sensitive restriction enzyme that cleaves both methylated and unmethylated CpG-sites, thereby cleaving the methylated nucleic acid.

Specific primers are added to the nucleic acid sample, and the nucleic acid is amplified by any conventional method. The presence of an amplified product in the sample treated with the methylation-sensitive restriction enzyme but absence of an amplified product in the sample treated with the isoschizomer of the methylation-sensitive restriction enzyme indicates that methylation has occurred at the nucleic acid region assayed. However, the absence of an amplified product in the sample treated with the methylation-sensitive restriction enzyme together with the absence of an amplified product in the sample treated with the isoschizomer of the methylation-sensitive restriction enzyme indicates that no methylation has occurred at the nucleic acid region assayed.

As used herein, the term "methylation-sensitive restriction enzyme" refers to a restriction enzyme (e.g., SmaI) that includes CG as part of its recognition site and has activity when the C is methylated as compared to when the C is not methylated. Non-limiting examples of methylation-sensitive restriction enzymes include MspI, HpaII, BssHII, BstUI and NotI. Such enzymes can be used alone or in combination.

Examples of other methylation-sensitive restriction enzymes include, but are not limited to SacII and EagI.

The isoschizomer of the methylation-sensitive restriction enzyme is a restriction enzyme that recognizes the same recognition site as the methylation-sensitive restriction enzyme but cleaves both methylated and unmethylated CGs. An example thereof includes MspI.

Primers of the present invention are designed to be "substantially" complementary to each strand of the locus to be amplified and include the appropriate G or C nucleotides as discussed above. This means that the primers must be sufficiently complementary to hybridize with their respective strands under polymerization reaction conditions. Primers of the present invention are used in the amplification process, which is an enzymatic chain reaction (e.g., PCR) in which that a target locus exponentially increases through a number of reaction steps. Typically, one primer is homologous with the negative (−) strand of the locus (antisense primer), and the other primer is homologous with the positive (+) strand (sense primer). After the primers have been annealed to denatured nucleic acid, the nucleic acid chain is extended by an enzyme such as DNA Polymerase I (Klenow), and reactants such as nucleotides, and, as a result, + and − strands containing the target locus sequence are newly synthesized. When the newly synthesized target locus is used as a template and subjected to repeated cycles of denaturing, primer annealing, and extension, exponential synthesis of the target locus sequence occurs. The resulting reaction product is a discrete nucleic acid duplex with termini corresponding to the ends of specific primers employed.

The amplification reaction is PCR which is commonly used in the art. However, alternative methods such as real-time PCR or linear amplification using isothermal enzyme may also be used. In addition, multiplex amplification reactions may also be used.

Detection of Differential Methylation—Bisulfate Sequencing Method

Another method for detecting a methylated CpG-containing nucleic acid comprises the steps of: bringing a nucleic acid-containing sample into contact with an agent that modifies unmethylated cytosine; and amplifying the CpG-containing nucleic acid in the sample using CpG-specific oligonucleotide primers, wherein the oligonucleotide primers distinguish between modified methylated nucleic acid and non-methylated nucleic acid and detect the methylated nucleic acid. The amplification step is optional and desirable, but not essential. The method relies on the PCR reaction to distinguish between modified (e.g., chemically modified) methylated DNA and unmethylated DNA. Such methods are described in U.S. Pat. No. 5,786,146 relating to bisulfite sequencing for detection of methylated nucleic acid.

Substrates

After the target nucleic acid region has been amplified, the nucleic acid amplification product can be hybridized to a known gene probe attached to a solid support (substrate) to detect the presence of the nucleic acid sequence.

As used herein, the term "substrate", when used in reference to a substance, structure, surface or material, means a composition comprising a nonbiological, synthetic, nonliving, planar or round surface that is not heretofore known to comprise a specific binding, hybridization or catalytic recognition site or a plurality of different recognition sites or a number of different recognition sites which exceeds the number of different molecular species comprising the surface, structure or material. Examples of the substrate include, but are not limited to, semiconductors, synthetic (organic) metals, synthetic semiconductors, insulators and dopants; metals, alloys, elements, compounds and minerals; synthetic, cleaved, etched, lithographed, printed, machined and microfabricated slides, devices, structures and surfaces; industrial polymers, plastics, membranes silicon, silicates, glass, metals and ceramics; and wood, paper, cardboard, cotton, wool, cloth, woven and nonwoven fibers, materials and fabrics; and amphibious surfaces.

It is known in the art that several types of membranes have adhesion to nucleic acid sequences. Specific non-limiting examples of these membranes include nitrocellulose or other membranes used for detection of gene expression such as polyvinylchloride, diazotized paper and other commercially available membranes such as GENE-SCREEN™, ZETAPROBET™ (Biorad), and NYTRANT™. Beads, glass, wafer and metal substrates are also included. Methods for attaching nucleic acids to these objects are well known in the art. Alternatively, screening can be done in a liquid phase.

Hybridization Conditions

In nucleic acid hybridization reactions, the conditions used to achieve a particular level of stringency will vary depending on the nature of the nucleic acids being hybridized. For example, the length, degree of complementarity, nucleotide sequence composition (e.g., GC/AT content), and nucleic acid type (e.g., RNA/DNA) of the hybridizing regions of the nucleic acids can be considered in selecting hybridization conditions. An additional consideration is whether one of the nucleic acids is immobilized, for example, on a filter.

An example of progressively higher stringency conditions is as follows: 2×SSC/0.1% SDS at room temperature (hybridization conditions); 0.2×SSC/0.1% SDS at room temperature (low stringency conditions); 0.2×SSC/0.1% SDS at 42° C. (moderate stringency conditions); and 0.1×SSC at about 68° C. (high stringency conditions).

Washing can be carried out using only one of these conditions, e.g., high stringency conditions, or each of the conditions can be used, e.g., for 10-15 minutes each, in the order listed above, repeating any or all of the steps listed. However, as mentioned above, optimal conditions will vary depending on the particular hybridization reaction involved, and can be determined empirically. In general, conditions of high stringency are used for the hybridization of the probe of interest.

Label

The probe of interest can be detectably labeled, for example, with a radioisotope, a fluorescent compound, a bioluminescent compound, a chemiluminescent compound, a metal chelator, or an enzyme. Appropriate labeling with such probes is widely known in the art and can be performed by any conventional method.

Kit

The present invention relates to a kit useful for the detection of abnormal cell growth in a subject. The kit of the present invention comprises a carrier means compartmentalized to receive a sample therein, one or more containers comprising a first container containing a reagent which sensitively cleaves unmethylated cytosine, a second container containing primers for amplification of a CpG-containing nucleic acid, and a third container containing a means to detect the presence of cleaved or uncleaved nucleic acid. Primers contemplated for use in accordance with the present invention include sequences set forth in SEQ ID NOS: 5 to 21, and any functional combination and fragments thereof. Functional combination or fragment is used as a primer to detect whether methylation has occurred on the region of the genome.

Carrier means are suited for containing one or more container means such as vials, tubes, and the like, each of the container means comprising one of the separate elements to be used in the method. In view of the description provided herein of the inventive method, those of skill in the art can readily determine the apportionment of the necessary reagents among the container means. For example, one of the container means can comprise a container containing a methylation-sensitive restriction enzyme. One or more container means can comprise a primer complementary to the nucleic acid locus of interest. In addition, one or more container means can contain an isoschizomer of the methylation sensitive restriction enzyme.

EXAMPLES

Hereinafter, the present invention will be described in further detail with reference to examples. It is to be understood, however, that these examples are for illustrative purposes only and are not to be construed to limit the scope of the present invention.

Example 1: Selection of Genes Hypermethylated in Lung Cancer Cell Line

Genes hypermethylated in lung cancer were selected in the following manner using the lung cancer cell line A549 (Korean Cell Line Bank (KCLB) 10185) and the normal lung cell line NHBE (Cambrex cc-2541).

First, 500 μg of gDNA of each cell line was sonicated to a size of 300-400 bp (Vibra Cell, SONICS), and methylated DNA was selectively enriched from each cell line using Methylcapture™ (Genomictree, Korea) according to the manufacturer's protocol. The enriched methylated DNAs were amplified using a GenomePlex® Complete Whole Genome Amplification Kit (Sigma), and then each of the amplified methylated DNAs derived from A549 and NHBE was labeled with Cy5-dUTP and Cy3-dUTP, respectively and mixed. Then, the DNAs were hybridized to a CpG microarray (Agilent) containing CpG probes representing about 27,800 CpG islands present in the human genome according to the Agilent' protocol, followed by scanning. Next, candidate genes hypermethylated in A549 were selected by a statistical technique (FIG. 1 and Table 1).

TABLE 1

List of genes hypermethylated in A549 lung cancer cell line

| Gene symbol | Genbank Acc. No. |
|---|---|
| ADAMTS20 | NM_175851 |
| BARHL2 | NM_020063 |
| C14orf39 | NM_174978 |
| CCDC8 | NM_032040 |
| CFL1-MUS81 | NM_005507 |
| CLDN11 | NM_005602 |
| CNIH3 | NM_152495 |
| CORO6 | NM_032854 |
| CPT1C | NM_152359 |
| DBX1 | NM_001029865 |
| DNMT3A | NM_153759 |
| DPP6 | NM_001936 |
| EN1 | NM_001426 |
| EPSTI1 | NM_033255 |
| GLUL | NM_001033056 |

TABLE 1-continued

List of genes hypermethylated in A549 lung cancer cell line

| Gene symbol | Genbank Acc. No. |
|---|---|
| GNAL | NM_002071 |
| GRHL2 | NM_024915 |
| HKR1 | NM_181786 |
| HLX1 | NM_021958 |
| HOXA11 | NM_005523 |
| HOXA5 | NM_019102 |
| HOXA6 | NM_024014 |
| HOXA7 | NM_006896 |
| HOXA9 | NM_152739 |
| HOXB5 | NM_002147 |
| HOXC11 | NM_014212 |
| HOXD12 | NM_021193 |
| HOXD8 | NM_019558 |
| IRX5 | NM_005853 |
| LHX1 | NM_005568 |
| LMX1A | NM_177398 |
| MEGF10 | NM_032446 |
| MOS | NM_005372 |
| PCDHGA12 | NM_003735 |
| PCDHGA5 | NM_032054 |
| PCDHGC3 | NM_032402 |
| PLCXD3 | NM_001005473 |
| POU4F3 | NM_002700 |
| PRAC | NM_032391 |
| PTGER4 | NM_000958 |
| RGMA | NM_020211 |
| RTKN | NM_033046 |
| TAC1 | NM_003182 |
| TBX5 | NM_080718 |
| TGIF2 | NM_021809 |
| TLX3 | NM_021025 |
| WNK3 | NM_020922 |
| WNT3 | NM_030753 |
| ZNF560 | NM_152476 |
| ZNF577 | NM_032679 |

Example 2: Selection of Genes Whose Expression was Repressed by Methylation in Lung Cancer Tissue To select genes whose expression is repressed by methylation in lung cancer tissue, microarray hybridization was performed using a standard protocol (Schena et al., Science, 270:467, 1995).

Tumor-adjacent tissue and tumor tissue were isolated from lung cancer patients so as to be paired, and total RNA was isolated from the tissues. In order to indirectly compare the gene expression levels of the paired tumor-adjacent normal tissues and tumor tissues, reference RNA (indirect comparison) was prepared. To construct the reference RNA, total RNA was isolated from the following eleven human cancer cell lines: lung cancer cell line A549 (Korean Cell Line Bank (KCLB) 10185), gastric cancer cell line AGS (KCLB 21739), renal cancer cell line Caki-2 (KCLB 30047), colon cancer cell line HCT116 (KCLB 10247), cervical cancer cell line Hela (KCLB 10002), blood cancer cell lines HK-60 (KCLB 10240) and HT1080 (KCLB 10121), breast cancer cell line MDA-MB231 (KCLB 30026), liver cancer cell line SK-hep1 (KCLB 30052), T-cell-derived cell line Molt-4 (KCLB 21582), and brain cancer cell line U-87MG (KCLB 30014). The total RNAs from the cell lines and lung tissue were isolated using Tri-Reagent (Sigma, USA).

To prepare the reference RNA, the equal amounts of the total RNAs from 11 cell lines were mixed and used as an internal control.

To compare the relative gene expression levels of the paired tumor-adjacent tissue and tumor tissue, the RNAs isolated from the tumor-adjacent normal tissues and the tumor tissues were compared with the reference RNA. For this purpose, 100 μg of each total RNA was labeled with Cy3-dUTP or Cy5-dUTP. The reference RNA was labeled with Cy3, and the RNAs isolated from lung tissues was labeled with Cy5. The Cy3- and Cy5-labeled cDNAs were purified using a PCR purification kit (Qiagen, Germany), mixed, and concentrated to a final volume of 27 μl using Microcon YM-30 (Millipore Corp., USA).

80 μl of a hybridization reaction solution (27 μl of the labeled cDNA target, 20 μl 20×SSC, 1% SDS 8%, 24 μl formamide (Sigma, USA) and 20 μg human Cot1 DNA (Invitrogen Corp., USA)) was heated at 100° C. for 2 minutes, and immediately hybridized to a human 22K oligonucleotide microarray (GenomicTree, Inc., Korea). The hybridization was carried out in a humidity-controlled Hyb-Chamber X (GenomicTree, Inc., Korea) at 42° C. for 12-16 hours. After completion of the hybridization, the microarray slide was scanned using Axon 4000B (Axon Instrument Inc., USA). The signal and background fluorescence intensities were calculated for each probe spot by averaging the intensities of every pixel inside the target region using GenePix Pro 4.0 software (Axon Instruments Inc., USA). Spots showing obvious abnormalities were excluded from analysis. All data normalization, statistical analysis and cluster analysis were performed using GeneSpring 7.2 (Agilent, USA).

To determine the relative difference in gene expression levels between the tumor-adjacent normal tissues and tumor tissues, statistical analysis (ANOVA ($p<0.01$) for indirect comparison was performed. From the results of the statistical analysis, 252 genes were down-regulated in the tumor tissues compared to the paired tumor-adjacent tissues.

Example 3: Selection of Genes Up-Regulated by Demethylation

In order to examine whether the expression of the genes identified in Example 1 would be regulated by the promoter methylation of the genes, the lung cancer cell lines A549 (KCLB 10185) and NCI-H358 (KCLB 90358) were treated with 200 nM of the demethylating agent 5-aza-2'-deoxycytidine (DAC, Sigma, USA) for 3 days. Total RNAs were isolated from untreated and treated cell lines by Tri-reagent.

To determine gene expression changes caused by DAC treatment, the transcript level was compared directly between the untreated and treated cell lines. As a result, it was seen that 376 genes showed elevated expression when treated with DAC compared with the control group not treated with DAC. 252 tumor repressor genes obtained in Example 1 were compared with the above 367 genes up-regulated two times or more by demethylation, and as a result, 18 concurrent genes therebetween were identified (FIG. 1).

Example 4: Identification of PCDHDGA12 Gene Hypermethylated in Lung Cancer

To confirm the presence of a CpG island in the promoter regions of the above-mentioned 18 genes, MethPrimer (http://itsa.ucsf.edu/~urolab/methprimer/index1.html) was used. Because 13 of the 18 genes had no CpG island, the 13 genes were excluded from the concurrent gene list. Accordingly, among the remaining 5 genes, the PCDHGA12 gene included in the 50 genes selected in the CpG microarray analysis in Example 1 was selected as a final lung cancer-related methylation biomarker. It could be seen that the selected PCDHGA12 gene was hypermethylated in the lung cancer cell line, down-regulated in lung tumor tissue, up-regulated in demethylation conditions, and contained CpG islands in the promoter, the 5'UTR and exon 1 regions (Table 2).

TABLE 2

Expression levels of PCDHGA12 gene in lung cancer tissue and lung cancer cell line

| | down-regulated degree in lung cancer tissue | | Re-expression levels in lung cancer cell line | |
| --- | --- | --- | --- | --- |
| gene | average fold change | p-value | A549 | NCI-H358 |
| PCDHGA12 | 0.26 | <0.01 | 2.0 | 7.3 |

Figure 2:
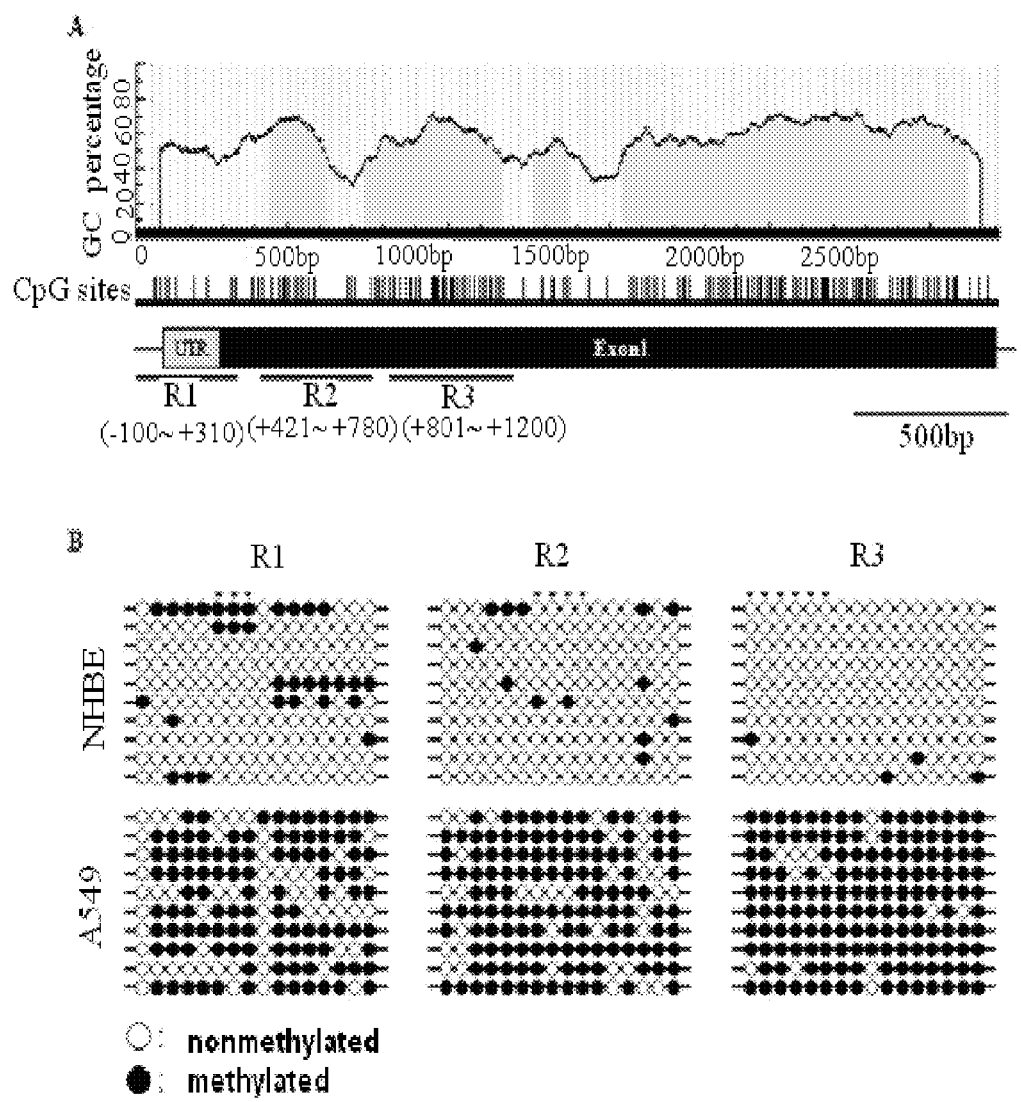
FIG. 2 shows the results of measuring the methylation degree of a gene region (A) and the methylation degree of UTR and exon regions (B) by bisulfite sequencing in order to determine the degree of methylation of PCDHGA12 in normal cell and lung cell lines.

Example 5: Identification of Hypermethylated Region of PCDHGA12 Gene in Lung Cancer (1) Identification by Bisulfite Clonal Sequencing The methylation status of the 5'UTR and exon 1 regions of PCDHGA12 gene was examined by bisulfite clonal sequencing using A549 and NHBE cell lines (FIG. 2A). In order to modify unmethylated cytosine to uracil using bisulfite, total genomic DNA was isolated from the normal cell line NHBE and the lung cancer cell line A549 (KCLB 10185), and 200 ng of the genomic DNA was treated with bisulfite using an EZ DNA methylation-Gold kit (Zymo Research, USA). When DNA is treated with bisulfite, unmethylated cytosine will be modified to uracil, and methylated cytosine will remain unchanged.

The DNA treated with bisulfite was eluted with 20 μl of sterile distilled water, and then 20 ng of the genomic DNA was amplified by PCR using primers having the base sequences shown in Table 3 below, thereby amplifying the R1, R2 and R3 regions of PCDHGA12 gene. The PCR amplification reaction was performed in the following conditions: 40 cycles each consisting of 1 min at 94° C.; 1 min at 66° C. and 1 min at 72° C.; and final extension of 10 min at 72° C.

TABLE 3

Bisulfite clonal sequencing primers

| Amplification region | SEQ ID NO | Base sequence (5' --> 3') |
| --- | --- | --- |
| R1 | 5 | TTTTTTTTGAAGAATAGTAGGTGGAGTTAT |
| | 6 | CAACCCCAAATCCCTAAAAATATC |
| R2 | 7 | GTTTGTTTTGTTGGGAATTTTTTTG |
| | 8 | AACCAAATAATAAACAACCTTTTCTTC |
| R3 | 9 | GAAAAGGTTGTTTATTATTTGGTTTTTA |
| | 10 | AAAACCTATTCCCTATCCAAAACTATATCT |

The DNA amplified by the PCR reaction was purified and cloned into a T/A cloning vector (Invitrogen, USA). 10 clones were selected from the clones obtained from each of the R1, R2 and R3 amplification products, and the base sequences thereof were analyzed to determine whether the regions were methylated. As a result, it was seen that the R1, R2 and R3 regions of A549 were highly methylated compared to NHBE (FIG. 2B). Particularly, the degree of methylation of the R3 region was most significantly different between A549 and NHBE.

(2) Identification by Pyrosequencing

Figure 3:
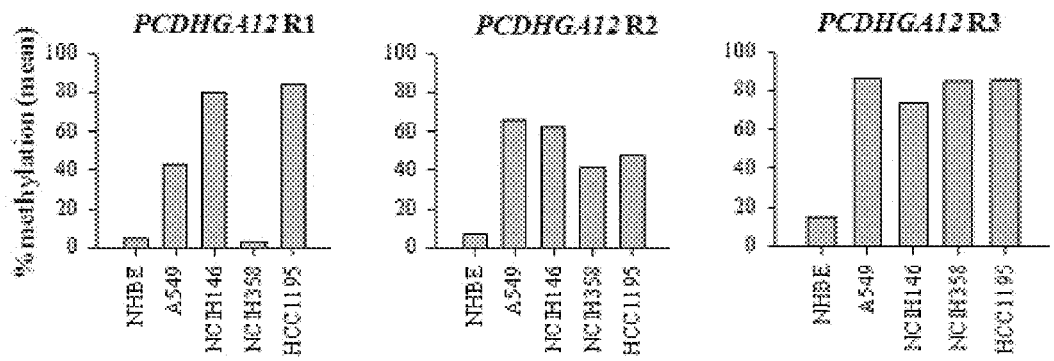
FIG. 3 shows the results of measuring the methylation degree of PCDHGA12 gene in normal cells and four kinds of lung cells by pyrosequencing.

The methylation of the 5'UTR and exon 1 regions of PCDHGA12 gene was examined by pyrosequencing using A549 and NHBE cell lines (FIG. 3). In order to modify unmethylated cytosine to uracil using bisulfite, total genomic DNA was isolated from the normal cell line NHBE and the lung cancer cell line A549 (KCLB 10185), and 200 ng of the genomic DNA was treated with bisulfite using an EZ DNA methylation-Gold kit (Zymo Research, USA). When DNA is treated with bisulfite, unmethylated cytosine will be modified to uracil, and methylated cytosine will remain unchanged.

The DNA treated with bisulfite was eluted with 20 μl of sterile distilled water and pyrosequenced. 20 ng of the genomic DNA treated with bisulfite was amplified by PCR. The PCR amplification reaction was performed in the following conditions: 40 cycles each consisting of 1 min at 94° C.; 1 min at 66° C. and 1 min at 72° C.; and final extension of 10 min at 72° C. The biotin-labeled template DNA was purified, and the base sequence thereof was analyzed using PyroMark ID (Biotage, Sweden). PCR and sequencing primers for each region for performing pyrosequencing for PCDHGA12 gene were designed using a PSQ assay design program (Biotage, USA). The PCR and sequencing primers for measurement of the promoter methylation of PCDHGA12 gene are shown in Table 4 below

TABLE 4

PCR and sequencing primers for pyrosequencing

| Amplification region | SEQ ID NO | Base sequences (5' --> 3') |
| --- | --- | --- |
| R1 | 11 | Biotin-GGGAGAGAAAAGTGGAGATTT |
|  | 12 | CTCCCAAAAATAATTCATTCCTAA |
|  | 13 | AACTATCTACTTTATACTTCAA |
| R2 | 14 | GGATAAAGTGAAAATATATGGAGTAG |
|  | 15 | Biotin-CCAAATAATAAACAACCTTTTCT |
|  | 16 | GTGAAAATGTAGTTATTGAG |
| R3 | 17 | AGAAAAGGTTGTTTATTATTTG |
|  | 18 | Biotin-TACCCAAAACCAAATTCTC |
|  | 19 | TGTTTATTATTTGGTTTTA |

In order to examine the hypermethylation of the three regions of PCDHGA12 gene in lung cancer cell lines, pyrosequencing was performed on the normal cell line NHBE (Cambrex CC-2541) and the lung cancer cell lines A549 (KCLB 10185), NCI-H146 (KCLB 30173), NCI-H358 (KCLB 90358) and HCC1195 (KCLB 71195) in the same manner as Example 5. As a result, it could be seen that the R1, R2 and R3 regions of PCDHGA12 gene were hypermethylated at high frequency in all the cancer cell lines. Particularly, the hypermethylation of the R3 region was high in all the lung cancer cell lines (FIG. 3).

Example 6: Measurement of Hypermethylation of PCDHGA12 Gene in Lung Cancer Tissues As shown in Examples above, the PCDHGA12 gene is hypermethylated in lung cancer cell lines, shows down-regulated expression in lung cancer tissue, reactivated in demethylation conditions, contains a CpG island in the 5'UTR and exon 1 regions, and is hypermethylated in the R1, R2 and R3 in various lung cancer cell lines. In order to verify whether the PCDHGA12 gene can be used as a biomarker for lung cancer diagnosis, a methylation assay was performed for the R1 and R3 regions of PCDHGA12 gene using lung tissues from five healthy persons, lung cancer tissues from 40 lung cancer patients, and normal tissues adjacent to the lung cancer tissues. The methylation assay was carried out using a pyrosequencing method according to the method described in Example 5.

Figure 4:
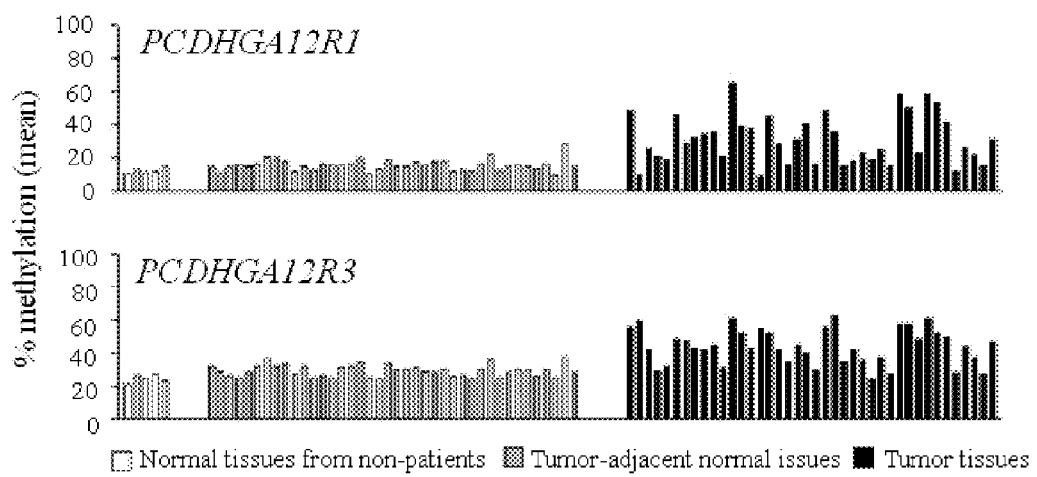
FIG. 4 shows the results of measuring the methylation degree of PCDHGA12 in five normal tissues and forty paired lung cancer tissues by pyrosequencing.

As a result, as shown in FIG. 4, the methylation of both the R1 and R3 regions of PCDHGA12 gene in the normal tissues-adjacent normal to the lung tumor tissues was similar to the methylation in the normal tissues from the healthy individuals, whereas a very high level of methylation was shown in the lung tumor tissues (p value=0.0001). Also, the methylation of the R1 region in the paired lung tumor tissues and the normal tissues adjacent thereto was shown to be high in 34 of 40 clinical samples (i.e., 85% of the clinical samples), and the methylation of the R3 region in these tissues was high in 36 of clinical samples (i.e., 90% of the clinical samples). These results suggest that lung cancer can be efficiently diagnosed by measuring the hypermethylation of PCDHGA12 gene.

Example 7: Measurement of Hypermethylation of PCDHGA12 in Non-Invasive Clinical Sample Sputum There are many reports that the DNA hypermethylation of various genes can also be detected in the sputum of lung cancer patients. Also, the use of sputum makes it possible to diagnose lung cancer at an early stage and the recurrence of lung cancer in a manner convenient for patients. Accordingly, the degree of hypermethylation of PCDHGA12 gene in cells contained in sputum samples was measured.

Figure 5:
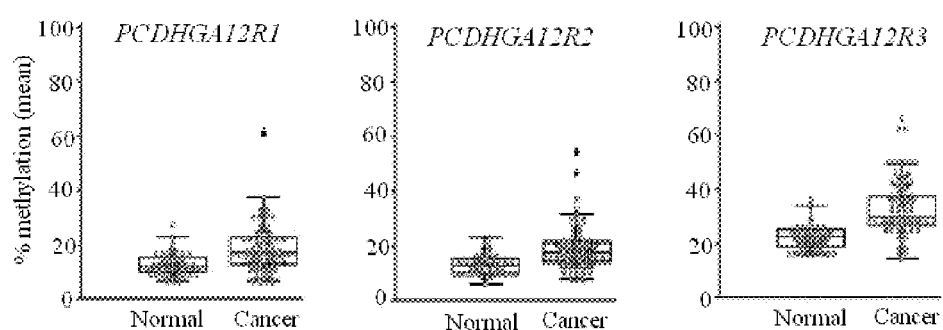
FIG. 5 shows the results of measuring the methylation of the genomic DNA of sputum cells of normal persons (n=51) and lung cancer patients (n=81).

Pyrosequencing for the R1, R2 and R3 regions of PCDHGA12 was performed on sputa from 51 healthy individuals and sputa from 81 lung cancer patients according to the method described in Example 5. As a result, it was seen that the hypermethylation of the R1, R2 and R3 regions of PCDHGA12 gene was higher in the septa of the lung cancer patients than in the septa of the healthy individuals (FIG. 5).

In addition, ROC (receiver operating characteristic) curve analysis was performed. As a result, when the methylation cut-off values of the R1, R2 and R3 regions were set to 13.49, 15.62 and 25.77, respectively, the sensitivities of the R1, R2 and R3 for the diagnosis of lung cancer in septa were as high as 74.1%, 70.4% and 86.4%, respectively, and the specificities of the R1, R2 and R3 regions for the diagnosis of lung cancer in septa were as high as 66.7%, 78.4% and 82.4% (Table 5). Accordingly, it is considered that, by detecting the DNA hypermethylation of PCDHGA12 gene in the non-invasive clinical sample sputum, it is possible to perform early diagnosis of lung cancer, diagnosis of the recurrence of lung cancer, monitoring after drug treatment, and monitoring of recurrence after surgery.

TABLE 5

Sensitivity and specificity of each region of PCDHGA12 gene to diagnosis of lung cancer in sputum sample

| Region | No. of methylation positive sample Cancer | No. of methylation negative samples Normal | Cut-off (%)[a] | AUC[b] | Sensitivity[c] | Specificity[c] |
|---|---|---|---|---|---|---|
| PCDHGA12 R1 | 60/81 | 17/51 | 13.49 | 0.725 | 74.1 | 66.7 |
| PCDHGA12 R2 | 57/81 | 11/51 | 15.62 | 0.762 | 70.4 | 78.4 |
| PCDHGA12 R3 | 70/81 | 9/51 | 25.77 | 0.874 | 86.4 | 82.4 |

[a]Cut-off of mean MtIs for each assay for discriminating cancer from normal were determined by Receiver Operating Characteristic (ROC) curve analysis;
[b]Area under the ROC curve was determined by ROC curve analysis;
[c]The sensitivity and specificity for detecting cancer from normal were determined by ROC curve analysis
†Dichotomous value of methylation status. When mean MtI was greater than a given cut-off for discriminating cancer from normal, it considered methylation positive, 1, while not in considered methylation negative, 0.

Example 8: Detection of Hypermethylation of PCDHGA12 Gene Using Methylated DNA-Specific Binding Protein The detection of hypermethylation of the PCDHGA12 R3 region having the highest sensitivity and specificity for the diagnosis of lung cancer was performed using a Methyl-Capture™ methylated DNA isolation kit (Genomictree, Korea). The MethylCapture™ methylated DNA isolation kit is capable of selectively isolating methylated DNA using MBD2bt protein binding specifically to methylated DNA and then measuring the methylation of the isolated DNA by PCR. Genomic DNA was extracted from cell lines and sputum samples, and each of the extracted DNAs was digested with MseI or sonicated to obtain a DNA fragment having a size of 200-600 bp. The DNA fragment was mixed with 2× binding buffer, competitor DNA and His-MBD2bt protein and allowed to react at 4° C. for 4 hours. Then, magnetic beads were added to the reaction solution, and the mixture was allowed to react at 4° C. for 45 minutes and washed five times with washing buffer to remove non-specifically bound DNA fragments. Finally, methylated DNA was isolated and purified from the washed solution using a Qiaquick PCR purification kit (Qiagen, USA). ⅕ volume of the purified DNA was taken and amplified by PCR using gene-specific primers, and the amplification product was electrophoresed to determine whether or not the DNA was methylated. The base sequences of the primers used for the amplification of the PCDHGA12 R3 regions are as follow:

SEQ ID NO 20: 5'-gaagaaaaggctgctcacca-3'

SEQ ID NO 21: 5'-tcgcatccagaaccatcac-3'

Figure 6:
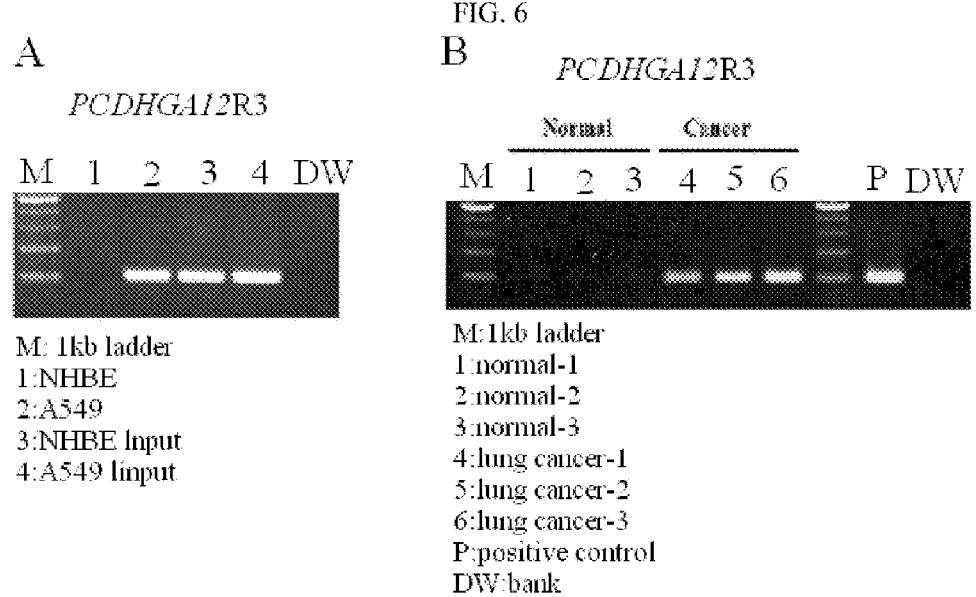
FIG. 6 shows the results of measuring the promoter methylation of PCDHGA12 gene using the sputum DNA of each of normal and lung cancer cell lines and normal and lung cancer patients.

As a result, no amplification product was observed in the normal cell line NHBE, and an amplification product of PCDHGA12 R3 was observed only in the lung cancer cell line A549, and thus lung cancer-specific methylation could be detected in the lung cancer cell line A549 (FIG. 6A). Also, the methylation of sputum cell genomic DNA in normal and lung cancer patients was measured and, as a result, no amplification product was observed in the sputum samples from three normal persons, but an amplification product was observed in all the sputum samples from three lung cancer patients (FIG. 6B). Accordingly, it could be confirmed that the methylation of PCDHGA12 R3 could be measured using the methylation-specific binding protein.

INDUSTRIAL APPLICABILITY

As described in detail above, the present invention provides the kit for lung cancer diagnosis which can determine the methylation status of CpG in the 5'UTR and exon regions of the lung cancer-specific marker gene. The diagnostic kit according to the present invention makes it possible to diagnose lung cancer at an early stage in an accurate and rapid manner compared to conventional methods and can be used for prognosis and monitoring of lung cancer.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

What is claimed is:

1. A method of detecting methylation of CpG of 5' UTR or exon 1 region of PCDHGA12, said method comprising:
    (a) obtaining a biological sample comprising DNA from lung cells from a patient;
    (b) obtaining a biological sample comprising DNA from normal lung cells from healthy controls;
    (c) treating the DNA from lung cells from the patient and normal lung cells with a bisulfite;
    (d) determining the level of methylation in the 5' UTR or exon 1 region of PCDHGA12 treated with a bisulfite in the sample from a patient by identifying CpG islands in the 5' UTR or exon 1 region of PCDHGA12 treated with the bisulfite and using primer(s) for amplifying a methylated fragment comprising the CpG of 5' UTR or exon 1 region of PCDHGA12 treated with a bisulfite; and
    (e) determining the level of methylation in the 5' UTR or exon 1 region of PCDHGA12 treated with a bisulfite in normal lung cells by identifying CpG islands in the 5' UTR or exon 1 region of PCDHGA12 treated with the bisulfite and using primer(s) for amplifying a methylated fragment comprising the CpG of 5' UTR or exon 1 region of PCDHGA12 treated with a bisulfite,
    wherein determining the level of methylation is performed using a primer pair that is:
        i) selected from the group consisting of SEQ ID NO. 5 and SEQ ID NO. 6, SEQ ID NO. 7 and SEQ ID NO. 8, and SEQ ID NO. 9 and SEQ ID NO. 10;
        ii) selected from the group consisting of SEQ ID NO. 11 to SEQ ID NO. 13, SEQ ID NO. 14 to SEQ ID NO. 16, and SEQ ID NO. 17 to SEQ ID NO. 19; or
        iii) a PCR primer pair of SEQ ID NO. 20 and SEQ ID NO. 21.

2. The method according to claim 1, wherein determining the level of methylation of the 5'UTR and exon 1 region of PCDHGA12 is performed in a DNA region having a sequence of SEQ ID NO: 1.

3. The method according to claim 1, wherein determining the level of methylation is performed in a DNA region having a sequence of SEQ ID NO: 2.

4. The method according to claim 1, wherein determining methylation of the exon 1 region of PCDHGA12 is performed in a DNA region having a sequence of SEQ ID NOs: 3 or 4.

5. The method according to claim 1, wherein determining methylation is performed using a method selected from the group consisting of PCR, methylation-specific PCR, real-time methylation-specific PCR, PCR using methylated DNA-specific binding proteins, quantitative PCR, a DNA chip, pyrosequencing and bisulfite sequencing.

6. The method according to claim 1, wherein the biological sample is selected from the group consisting of a tissue, sputum, and blood from a patient suspected of cancer or a subject to be diagnosed.

* * * * *

UNITED STATES PATENT AND TRADEMARK OFFICE
CERTIFICATE OF CORRECTION

PATENT NO. : 9,850,540 B2  
APPLICATION NO. : 12/922184  
DATED : December 26, 2017  
INVENTOR(S) : Sungwhan An Page 1 of 1

It is certified that error appears in the above-identified patent and that said Letters Patent is hereby corrected as shown below:

On the Title Page

Inventors item (75): "Young Ho Moon, Daejean (KR)" should be --Young Ho Moon, Daejeon (KR)--.

In the Specification

Column 1, Line 63: "and its utility also limiter" should be --and its utility also limited--.

Column 2, Line 2: "and functional loss oncogenes" should be --and functional loss of oncogenes--.

Column 4, Line 2: "five normal tissues and forty paired" should be --five normal tissues and four paired--.

Column 12, Lines 16-17: "ZETAPROBET™ (Biorad), and NYTRANT™" should be --ZETAPROBE™ (Biorad), and NYTRAN™--.

Signed and Sealed this  
Twenty-seventh Day of March, 2018

Andrei Iancu  
*Director of the United States Patent and Trademark Office*